United States Patent [19]

Palfreyman et al.

[11] Patent Number: 4,965,288

[45] Date of Patent: Oct. 23, 1990

[54] INHIBITORS OF LYSYL OXIDASE

[75] Inventors: Michael G. Palfreyman, Cincinnati; Philippe Bey, Cincinnati; Ian A. McDonald, Loveland, all of Ohio

[73] Assignee: Merrell Dow Pharmaceuticals Inc., Cincinnati, Ohio

[21] Appl. No.: 409,270

[22] Filed: Sep. 19, 1989

Related U.S. Application Data

[63] Continuation of Ser. No. 160,364, Feb. 25, 1988, abandoned.

[51] Int. Cl.$^5$ .................... A61K 31/135; A61K 31/15
[52] U.S. Cl. ...................... 514/649; 514/671
[58] Field of Search ................ 514/649, 671

[56] References Cited

U.S. PATENT DOCUMENTS 4,454,158  6/1984  Bey ........................................ 514/649
4,650,907  3/1987  Bey et al. ............................. 564/509

FOREIGN PATENT DOCUMENTS 2162518  2/1986  United Kingdom ................ 514/649

Primary Examiner—Douglas W. Robinson
Assistant Examiner—Zohreh A. Fay
Attorney, Agent, or Firm—Michael J. Sayles

[57] ABSTRACT

This invention relates to certain inhibitors of lysyl oxidase and their use in the treatment of diseases and conditions associated with the abnormal deposition of collagen.

7 Claims, No Drawings

INHIBITORS OF LYSYL OXIDASE

This is a continuation of application Ser. No. 160,364, filed Feb. 25, 1988 now abandoned.

Collagen is the main protein of skin, tendon, bone, cartilage, and connective tissue. Collagen molecules are characterized by a triple-stranded helical structure made up of α-chains, and each collagen molecule is about 300 nm long and about 1.5 nm in diameter. Precursor pro-α-chains having certain residues called extension peptides not present in the final product, are the initial products of RNA mediated peptide synthesis within fibroblasts. These pro-α-chains first assemble into triple-stranded procollagen molecules intracellularly and the component lysine and proline residues are hydroxylated and subsequently glycosylated. During secretion, the extension peptides of the procollagen molecules are cleaved and collagen is formed. After secretion, collagen assembles into microfibrils and ultimately fibrils.

Strength of collagen is provided by crosslinking between various lysine residues both within a fibril and between fibrils. The first step of the crosslinking process is the deamination of lysine and hydroxylysine residues by extracellular lysyl oxidase to produce aldehyde groups. These highly reactive groups then form the crosslinks. The amount and type of crosslinking varies greatly according to the strength requirements of the various tissue types. If crosslinking is inhibited, the tissue becomes fragile and accordingly tears quite easily. Certain serious medical conditions are associated with the lack of collagen crosslinking such as Ehlers-Danlos Syndrome and Marfan's syndrome. While collagen crosslinking is essential, in certain instances it is desirable to prevent or reduce crosslinking such as in conditions and diseases characterized by defects in collagen metabolism such as occurs in various fibrotic conditions, for example, lung fibrosis, as well as in proliferative vitreo retinopathy, surgical scarring, systemic sclerosis, scleroderma, and keloids.

Certain inhibitors of collagen crosslinking are known such as penicillamine and beta-aminopropionitrile (BAPN). BAPN is known to prevent crosslinking specifically because of its ability to inhibit lysyl oxidase. Both penicillamine and BAPN have been studied extensively in animals and in humans for their effects on conditions associated with the abnormal deposition of collagen. The applicants have now discovered that certain halogenated allyl amines are inhibitors of lysyl oxidase and are useful in the treatment of diseases and conditions associated with abnormal collagen deposition.

SUMMARY OF THE INVENTION

Compounds of formula 1

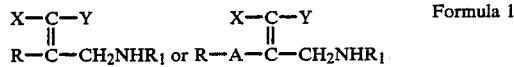
Formula 1 wherein
X and Y are identical and are each either a fluoro, chloro, or bromo group or one of X and Y is a hydrogen and the other is a fluoro, chloro, or bromo group;
$R_1$ is a hydrogen, or a $(C_1-C_4)$alkyl group;
A is a divalent radical group selected from

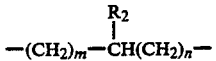

wherein
$R_2$ is hydrogen, methyl, or ethyl, and m and n, independently, are an integer from 0 to 16, provided that m+n cannot be greater than 17;

wherein
D is oxygen or sulfur, p is an integer of from 0 to 16, and q is an integer of from 1 to 16, provided that m+n cannot be greater than 17; and

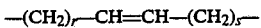

wherein
s is an integer of from 1 to 16 and r is an integer of from 0 to 16, provided that r+s cannot be greater than 16; and
R is a methyl group, a phenyl, or a phenyl substituted with one or two members of the group $(C_{14}\ C_5)$alkyl, $(C_1-C_5)$alkoxy, hydroxy, chloro, bromo, fluoro, iodo, trifluoromethyl, nitro, $(C_1-C_5)$alkylcarbonyl, benzoyl, or phenyl; or
R is 1- or 2-naphthyl; 1-, 2-, or 3-indenyl; 1-, 2-, or 9-fluorenyl; 1-, 2-, or 3-piperidinyl; 2- or 3- pyrrolyl; 2- or 3-thienyl; 2- or 3-furanyl; 2- or 3- indolyl; 2- or 3-thianaphthylenyl; or 2- or 3- benzofuranyl;
or a pharmaceutically acceptable salt thereof.

DETAILED DESCRIPTION OF THE INVENTION

Illustrative examples of divalent groups represented by A are $-CH_2-$, $-(CH_2)_2-$, $-(CH_2)_3-$, $-(CH_2)_4-$, $-(CH_2)_5-$, $-CH_2S-(CH_2)_2-$, $-CH_2O(CH_2)_2-$, and $-CH=CH-CH_2-$. The term "$(C_1-C_5)$alkyl" means straight- and branched-chain alkyl groups. Illustrative examples of $(C_1-C_5)$alkyl groups are methyl, ethyl, n-propyl, isopropyl, n-butyl, isobutyl, tert-butyl, and n-pentyl. The term "$(C_1C_5)$alkoxy" means straight- and branched-chain alkoxy groups. Illustrative examples of $(C_1-C_5)$alkoxy are methoxy, ethoxy, n-propoxy, isopropoxy, n-butoxy, isobutoxy, and n-pentoxy. The term "$(C_1-C_5)$alkylcarbonyl" means both straight- and branched-chain alkylcarbonyl groups. Examples of such groups are acetyl, propionyl, and n-butyryl.

It will be apparent to those skilled in the art that the compounds of Formula 1 contain one or two double bonds, and therefore geometric isomerism is possible, i.e. at the allyl amine double bond and in the A group olefinic bond if present. In naming the compounds of this invention the prefixes "(E)" and "(Z)" are used in the conventional manner to indicate stereochemistry at the double bonds. If no stereochemical designation is given, both the substantially pure isomers or mixtures are intended. In those compounds wherein one of X and Y is a fluoro, chloro, or bromo group and the other is a hydrogen, applicants prefer those compounds wherein the halo group is oriented cis to the $-R$ or $-A-R$ group.

The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intented to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. The salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Illustrative examples of the compounds of formula 1 are:

2-isobutyl-3-fluoro-, chloro-, or bromo-allylamine; 2-isopropyl-3-fluoro-, chloro-, or bromo-allylamine; 2-(9-octadecenyl)-3-fluoro-, chloro-, or bromo-allylamine;
2-(3-methyl-3-butenyl)-3-fluoro-, chloro-, or bromo-allylamine;
2-(4-methoxy-2-butenyl)-3-fluoro-, chloro-, or bromo-allylamine;
2-sec-butyl-3-fluoro-, chloro-, or bromo-allylamine;
2-butyl-3-fluoro-, chloro-, or bromo-allylamine;
2-hexyl-3-fluoro-, chloro-, or bromo-allylamine;
2-heptyl-3-fluoro-, chloro-, or bromo-allylamine;
2-ethoxymethyl-3-fluoro-, chloro-, or bromo-allylamine;
2-thioethoxymethyl-3-fluoro-, chloro-, or bromo-allylamine;
2-phenyl-3-fluoro-, chloro-, or bromo-allylamine;
2-(2-methoxyphenyl)-3-fluoro-, chloro-, or bromo-allylamine;
2-(3-methoxyphenyl)-3-fluoro-, chloro-, or bromo-allylamine;
2-(4-methoxyphenyl)-3-fluoro-, chloro-, or bromo-allylamine;
2-(2,3-dimethoxyphenyl)-3-fluoro-, chloro-, or bromo-allylamine;
2-(2,4-dimethoxyphenyl)-3-fluoro-, chloro-, or bromo-allylamine;
2-(2,5-dimethoxyphenyl)-3-fluoro-, chloro-, or bromo-allylamine;
2-(2,6-dimethoxyphenyl)-3-fluoro-, chloro-, or bromo-allylamine;
2-(3,4-dimethoxyphenyl)-3-fluoro-, chloro-, or bromo-allylamine;
2-(3,5-dimethoxypenyl)-3-fluoro-, or chloro-, or bromo-allylamine;
2-(2-hydroxyphenyl)-3-fluoro-, chloro-, or bromo-allylamine;
2-(3-hydroxyphenyl)-3-fluoro-, chloro-, or bromo-allylamine;
2-(4-hydroxyphenyl)-3-fluoro-, chloro-, or bromo-allylamine;
2-(2,3-dihydroxyphenyl)-3-fluoro-, chloro-, or bromo-allylamine;
2-(2,4-dihydroxyphenyl)-3-fluoro-, chloro-, or bromo-allylamine;
2-(2,5-dihydroxyphenyl)-3-fluoro-, chloro-, or bromo-allylamine;
2-(2,6-dihydroxyphenyl)-3-fluoro-, chloro-, or bromo-allylamine;
2-(3,4-dihydroxyphenyl)-3-fluoro-, chloro-, or bromo-allylamine;
2-(3,5-dihydroxyphenyl)-3-fluoro-, chloro , or bromo-allylamine;
2-phenyl-3,3-difluoro-, dichloro-, or dibromo-allylamine;
2-(2-methoxyphenyl)-3,3-difluoro-, dichloro-, or dibromo-allylamine;
2-(3-methoxyphenyl)-3,3-difluoro-, dichloro-, or dibromo-allylamine;
2-(4-methoxyphenyl)-3,3-difluoro-, dichloro-, or dibromo-allylamine;
2-(2,3-dimethoxyphenyl)-3,3-difluoro-, dichloro-, or dibromo-allylamine;
2-(2,4-dimethoxyphenyl)-3,3-difluoro-, dichloro-, or dibromo-allylamine;
2-(2,5-dimethoxyphenyl)-3,3-difluoro-, dichloro-, or dibromo-allylamine;
2-(2,6-dimethoxyphenyl)-3,3-difluoro-, dichloro-, or dibromo-allylamine;
2-(3,4-dimethoxyphenyl)-3,3-difluoro-, dichloro-, or dibromo-allylamine;
2-(3,5-dimethoxyphenyl)-3,3-difluoro-, dichloro-, or dibromo-allylamine;
2-(2-hydroxyphenyl)-3,3-difluoro-, dichloro-, or dibromo-allylamine;
2-(3-hydroxyphenyl)-3,3-difluoro-, dichloro-, or dibromo-allylamine;
2-(4-hydroxyphenyl)-3,3-difluoro-, dichloro-, or dibromo-allylamine;
2-(2,3-dihydroxyphenyl)-3,3-difluoro-, dichloro-, or dibromo-allylamine;
2-(2,4-dihydroxyphenyl)-3,3-difluoro-, dichloro-, or dibromo-allylamine;
2-(2,5-dihydroxyphenyl)-3,3-difluoro-, dichloro-, or dibromo-allylamine;
2-(2,6-dihydroxyphenyl)-3,3-difluoro-, dichloro-, or dibromo-allylamine;
2-(3,4-dihydroxyphenyl)-3,3-difluoro-, dichloro-, or dibromo-allylamine;
2-(3,5-dihydroxyphenyl)-3,3-difluoro-, dichloro-, or dibromo-allylamine;
2-benzyl-3-fluoro-, chloro-, or bromo-allylamine;
2-phenethyl-3-fluoro-, chloro-, or bromo-allylamine;
2-(2-methoxybenzyl)-3-fluoro-, chloro-, or bromo-allylamine;
2-(3-methoxybenzyl)-3-fluoro-, chloro-, or bromo-allylamine;
2-(4-methoxybenzyl)-3-fluoro-, chloro-, or bromo-allylamine;
2-(2,3-dimethoxybenzyl)-3-fluoro-, chloro-, or bromo-allylamine;
2-(2,4-dimethoxybenzyl)-3-fluoro-, chloro-, or bromo-allylamine;

2-(2,5-dimethoxybenzyl)-3-fluoro-, chloro-, or bromo-allylamine;

2-(2,6-dimethoxybenzyl)-3-fluoro-, chloro-, or bromo-allylamine;

2-(3,4-dimethoxybenzyl)-3-fluoro-, chloro-, or bromo-allylamine;

2-(3,5-dimethoxybenzyl)-3-fluoro-, chloro-, or bromo-allylamine;

2-(2-hydroxybenzyl)-3-fluoro-, chloro-, or bromo-allylamine;

2-(3-hydroxybenzyl)-3-fluoro-, chloro-, or bromo-allylamine;

2-(4-hydroxybenzyl)-3-fluoro-, chloro-, or bromo-allylamine;

2-(2,3-dihydroxybenzyl)-3-fluoro-, chloro-, or bromo-allylamine;

2-(2,4-dihydroxybenzyl)-3-fluoro-, chloro-, or bromo-allylamine;

2-(2,5-dihydroxybenzyl)-3-fluoro-, chloro-, or bromo-allylamine;

2-(2,6-dihydroxybenzyl)-3-fluoro-, chloro-, or bromo-allylamine;

2-(3,4-dihydroxybenzyl)-3-fluoro-, chloro-, or bromo-allylamine;

2-(3,5-dihydroxybenzyl)-3-fluoro-, chloro-, or bromo-allylamine;

2-benzyl-3,3-difluoro-, dichloro-, or dibromo-allylamine;

2-(2-methoxybenzyl)-3,3-difluoro-, dichloro-, or dibromo-allylamine;

2-(3-methoxybenzyl)-3,3-difluoro-, dichloro-, or dibromo-allylamine;

2-(4-methoxybenzyl)-3,3-difluoro-, dichloro-, or dibromo-allylamine;

2-(2,3-dimethoxybenzyl)-3,3-difluoro-, dichloro-, or dibromo-allylamine;

2-(2,4-dimethoxybenzyl)-3,3-difluoro-, dichloro-, or dibromo-allylamine;

2-(2,5-dimethoxybenzyl)-3,3-difluoro-, dichloro-, or dibromo-allylamine;

2-(2,6-dimethoxybenzyl)-3,3-difluoro-, dichloro-, or dibromo-allylamine;

2-(3,5-dimethoxybenzyl)-3,3-difluoro-, dichloro-, or dibromo-allylamine;

2-(2-hydroxybenzyl)-3,3-difluoro-, dichloro-, or dibromo-allylamine;

2-(3-hydroxybenzyl)-3,3-difluoro-, dichloro-, or dibromo-allylamine;

2-(4-hydroxybenzyl)-3,3-difluoro-, dichloro-, or dibromo-allylamine;

2-(2,3-dihydroxybenzyl)-3,3-difluoro-, dichloro-, or dibromo-allylamine;

2-(2,4-dihydroxybenzyl)-3,3-difluoro-, dichloro-, or dibromo-allylamine;

2-(2,5-dihydroxybenzyl)-3,3-difluoro-, dichloro-, or dibromo-allylamine;

2-(2,6-dihydroxybenzyl)-3,3-difluoro-, dichloro-, or dibromo-allylamine;

2-(3,4-dihydroxybenzyl)-3,3-difluoro-, dichloro-, or dibromo-allylamine;

2-(3,5-dihydroxybenzyl)-3,3-difluoro-, dichloro-, or dibromo-allylamine;

2-phenoxymethyl-3-fluoro-, chloro-, or bromo-allylamine;

2-(4-methoxyphenoxymethyl)-3-fluoro-, chloro-, or bromo-allylamine;

2-(2,4-dimethoxyphenoxymethyl)-3-fluoro-, chloro-, or bromo-allylamine;

2-(2,6-dimethoxyphenoxymethyl)-3-fluoro-, chloro-, or bromo-allylamine;

2-(3,4-methylenedioxyphenoxymethyl)-3-fluoro-, chloro-, or bromo-allylamine;

2-(3-hydroxyphenoxymethyl)-3-fluoro-, chloro-, or bromo-allylamine;

2-(4-hydroxyphenoxymethyl)-3-fluoro-, chloro-, or bromo-allylamine;

2-(2,3-dihydroxyphenoxymethyl)-3-fluoro-, chloro-, or bromo-allylamine;

2-(2,4-dihydroxyphenoxymethyl)-3-fluoro-, chloro-, or bromo-allylamine;

2-(2-methylphenoxymethyl)-3-fluoro-, chloro-, or bromo-allylamine;

2-(2-chlorophenoxymethyl)-3-fluoro-, chloro-, or bromo-allylamine;

2-(4-chlorophenoxymethyl)-3-fluoro-, chloro-, or bromo-allylamine;

2-(4-trifluoromethylphenoxymethyl)-3-fluoro-, chloro-, or bromo-allylamine;

2-thiophenoxmethyl-3-fluoro-, chloro-, or bromo-allylamine;

2-(4-methoxythiophenoxymethyl)-3-fluoro-, chloro-, or bromo-allylamine;

2-(2,4-dimethoxythiophenoxymethyl)-3-fluoro-, chloro-, or bromo-allylamine;

2-(2,4-dichlorothiophenoxymethyl)-3-fluoro-, chloro-, or bromo-allylamine;

2-(4-hydroxythiophenoxymethyl)-3-fluoro-, chloro-, or bromo-allylamine;

2-(1-naphthyloxymethyl)-3-fluoro-, chloro-, or bromo-allylamine; and 2-(2-naphthyloxymethyl)-3-fluoro-, chloro-, or bromo-allylamine;

Presently preferred compounds of formula 1 are those in which one or both of X and Y are a chloro or bromo group.

Many of the compounds of this invention are known and the preparation of these compounds is described in, for example, U.S. Pat. No. 4,454,158, granted June 12, 1984, British Patent Application Number 2,162,518, published Feb. 5, 1986, and U.S. Pat. No. 4,650,907, granted Mar. 17, 1987. The preparation of those compounds not specifically described in these publications can readily be prepared using analogous procedures.

The ability of the compounds of this invention to be useful in the treatment of diseases and conditions associated with defects in collagen metabolism such as occurs in various fibrotic conditions, for example, lung fibrosis, as well as in proliferative vitreo retinopathy, surgical scarring, systemic sclerosis, scleroderma, and keloids can be demonstrated by the ability of the compounds to inhibit lysyl oxidase. The lysyl oxidase inhibition activity for representative members of the compounds of this invention is tabulated in Example 1.

The amount of the active ingredient to be administered can vary widely according to the particular dosage unit employed, the period of treatment, the age and sex of the patient treated and the nature and extent of the disorder treated. The total amount of the active ingredient to be administered will generally range from about 5 mg to about 500 mg per day. A unit dosage may contain from 25 to 500 mg of active ingredient, and can be taken one or more times per day. The active compound of formula 1 can be administered with a pharmaceutical carrier using conventional dosage unit forms either orally, parenterally, or topically. In the case of abnormal collagen deposition of the skin, topical administration to the diseased site is preferred, and in the case of abnormal collagen deposition to internal sites, local administration where possible and practical is preferred. Where local or topical application is not possible, systemic administration should be of short duration lasting, for example, for only a few days, and the patient should be closely monitored for adverse affects.

Coadministration of a compound of formula 1 with penicillamine, a compound known to be useful in the treatment of diseases and conditions characterized by abnormal collagen deposition but known to function by other than the inhibition of lysyl oxidase, is expected to be advantagous. The effective dosage of a compound of formula 1 when co-administered with penicillamine is expected to be less than the effective dosage when administered alone and will depend on the quantity and frequency of penicillamine co-administered. Therapy should be instituted at lower dosages of the formula 1 compound and of penicillamine than would be used in the absence of co-administration and the dosages thereafter altered to acheive the desired effect. The amount of compound of formula 1 as compared to the amount of penicillamine can vary from, for example, 1:1 to be administered substantially at the same time as, prior to, or after administration of penicillamine.

For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intented to assist the break-up and dissolution of the tablet following administration such as potato starch, alginic acid, corn starch, and guar gum, lubricants intented to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intented to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention are preferably administered topically when used to treat a disease or condition characterized by abnormal collagen deposition of the skin. Any of the above described liquid formulations, including gels and ointments, may take the form of skin lotions and creams and may also contain emollients, perfumes, astringents, shaving lotions, colognes, cosmetic foundations, and similar preparations. In general a topical composition of this invention will contain from about 0.01 g to about 5 g of a compound of formula 1 per 100 ml of the composition.

The following examples illustrate the activity and formulation of the compounds of this invention.

EXAMPLE 1

LYSYL OXIDASE INHIBITION STUDIES

Lysyl oxidase preparation is obtained from bovine aorta by the procedures modified from M. A. Williams and H. M. Kagan, *Anal. Biochem.* 149, 430–437 (1985) and H. M. Kagan and K. A. Sullivan, *Methods in Enzyml.* 82, 637–650 (1982). The aorta is obtained fresh on the day of the enzyme preparation and is maintained at 4° C. for the duration of its use in the experiments. The aorta is ground fine and is homogenized for 90 seconds in buffer (2.5 ml of a buffer consisting of 16 mM potassium phosphate and 1 mM phenylmethylsulfonyl fluoride/g of tissue) with 0.15 M NaCl added, then the mixture is centrifuged (20 minutes at 11,000×g. The homogenization followed by centrifugation procedure is repeated with buffer plus 0.15 M NaCl, buffer alone, and buffer plus 1M urea. After homogenization in 1M urea, the mixture is stirred for 1 hour prior to centrifugation. The resulting pellet is homogenized in buffer plus 4M urea, stirred for 18 hours, and centrifuged. The supernatant with lysyl oxidase activity is saved. The tissue is homogenized in buffer plus 4M urea, stirred overnight, and centrifuged twice more. The supernatants with lysyl oxidase activity are saved.

The assay is adopted from that of P. C. Trackman, et al., *Anal. Biochem.* 113, 336–342 (1981). Each assay consists of two tubes, one that contains 0.2 mM β-aminopropionitrile, BAPN, from the start and one to which BAPN is added to quench the reaction. Lysyl oxidase preparation (0.150 ml), urea (0.300 ml, 4M), buffer (0.930 ml, 200 mM borate at pH=8.2), homovanillic acid (0.020 ml of 50 mM solution), and horseradish peroxidase (0.010 ml of Sigma Type II at 5 mg/ml protein) are incubated for 2 minutes at 55° C. in a test tube. Cadaverine (0.100 ml of 150 mM) and test compound, if any, is added and the incubation continued at 55° C. for an additional 10 minutes. The test tubes containing this mixture are then cooled in a ice bath after adding BAPN to any tubes not containing it. The difference in fluorescence (excitation 315 nm and emission 425 nm) between corresponding tubes that received BAPN at 0 minutes and at 10 minutes is a measure of enzyme activity. A standard curve to determine the amount of cadaverine converted by lysyl oxidase is prepared as follows. Assay mixtures containing BAPN are made up as described and known amounts of hydrogen peroxide are added simultaneously with cadaverine and the fluorescence changes after 10 minutes reaction are determined.

Using this method the lysyl oxidase inhibiting activity expressed as $IC_{50}$ (inhibitory concentration), that is the concentration of test compound required to inhibit the enzyme activity by 50 per cent, was determined for various compounds of this invention. The results are shown in Table 1.

TABLE 1
LYSYL OXIDASE INHIBITION ACTIVITY
OF HALOGENATED ALLYLAMINES

| TEST COMPOUND | $IC_{50}$ (M) |
|---|---|
| (E)-2-(4-Fluorophenethyl)-3-fluoroallylamine | $1 \times 10^{-10}$ |
| (E)-2-(3,4-Dimethoxyphenylpropyl)-3-fluoroallylamine | $1 \times 10^{-10}$ |
| (E)-2-(Thiophenoxymethyl)-3-fluoroallylamine | $1 \times 10^{-10}$ |
| (E)-2-Phenyl-3-fluoroallylamine | $1 \times 10^{-9}$ |
| (Z)-2-(3,4-Dichlorophenoxymethyl)-3-fluoroallylamine | $1 \times 10^{-9}$ |
| (Z)-2-(2-Thienyl)-3-fluoroallylamine | $1 \times 10^{-9}$ |
| (E)-2-Isobutyl-3-fluoroallylamine | $1 \times 10^{-8}$ |
| (E)-2-Undecyl-3-fluoroallylamine | $1 \times 10^{-7}$ |
| (E)-2-(3,4-Dimethoxyphenyl)-3-fluoroallylamine | $1 \times 10^{-7}$ |
| (E)-N-Ethyl-2-(3,4-dimethoxyphenyl)-3-fluoroallylamine | $1 \times 10^{-6}$ |
| (E)-2-Phenethyl-3-chloroallylamine | $1 \times 10^{-8}$ |
| (E)-2-Isobutyl-3-chloroallylamine | $1 \times 10^{-7}$ |
| (E)-2-Phenyl-3-chloroallylamine | $1 \times 10^{-7}$ |

We claim:

1. A method of treating diseases and conditions associated with the abnormal deposition of collagen in a patient in need thereof which comprises administering to the patient a lysyl oxidase inhibiting amount of penicillamine together with an effective amount of a compound of the formula

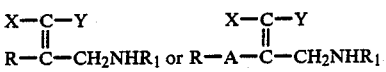

wherein
X and Y are identical and are each either a fluoro, chloro, or bromo group or one of X and Y is a hydrogen and the other is a fluoro, chloro, or bromo group;
$R_1$ is a hydrogen or a $(C_1-C_4)$alkyl group;
A is a divalent radical group selected from

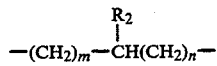

wherein
$R_2$ is hydrogen, methyl, or ethyl, and m and n, independently, are an integer from 0 to 16, provided that m+n cannot be greater than 17;

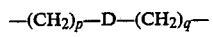

wherein
D is oxygen or sulfur, p is an integer of from 0 to 16, and q is an integer of from 1 to 16, provided that m+n cannot be greater than 17; and

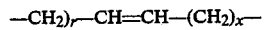

wherein
s is an integer of from 1 to 16 and r is an integer of from 0 to 16, provided that r+s cannot be greater than 16; and
R is a methyl group, a phenyl, or a phenyl substituted with one or two members of the group $(C_1-C_5)$alkyl, $(C_1-C_5)$alkoxy, hydroxy, chloro, bromo, fluoro, iodo, trifluoromethyl, nitro, $(C_1-C_5)$alkylcarbonyl, benzoyl, or phenyl;
or a pharmaceutically acceptable salt thereof.

2. A method of claim 1 wherein X and Y are each a chloro or bromo group or wherein one of X and Y is a chloro or bromo group and the other is a hydrogen.

3. A method of one of claims 1 or 2 wherein R is a phenyl or a phenyl mono- or di-substituted by $(C_1-C_5)$alkyl, $(C_1-C_5)$alkoxy, hydroxy, chloro, bromo, fluoro, iodo, trifluoromethyl, nitro, $(C_1-C_5)$alkylcarbonyl, benzoyl, or phenyl.

4. A method of one of claims 1 or 2 wherein R is a methyl group and A, if present, is a divalent radical selected from

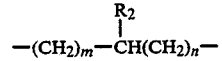

wherein
$R_2$ is hydrogen, methyl, or ethyl, and m and n, independently, are an integer from 0 to 16, provided that m+n cannot be greater than 17;

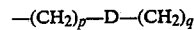

wherein

D is oxygen or sulfur, p is an integer of from 0 to 16, and q is an integer from 1 to 16, provided that m+n cannot be greater than 17.

5. A method of one of claims 1 or 2 wherein R is a methyl group and A, if present, is a divalent radical selected from

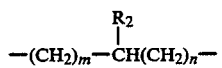

wherein $R_2$ is hydrogen methyl, or ethyl, m is an integer of from 0 to 16, and n is zero; and

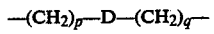

wherein
D is oxygen or sulfur, p is an integer of from 0 to 16, and q is the integer 1.

6. A method of claim 2 wherein R is a phenyl, methoxyphenyl, dimethoxyphenyl, hydroxyphenyl, dihydroxyphenyl, chlorophenyl, or dichlorophenyl.

7. A method of claim 6 wherein an A group is not present or wherein A is a methylene group or a group of the formulae —SCH$_2$— or —OCH$_2$—.

* * * * *